United States Patent [19]

Press et al.

[11] Patent Number: 4,885,300
[45] Date of Patent: Dec. 5, 1989

[54] 4-SUBSTITUTED PYRAZOLO[3,4-D]PYRIMIDINE DERIVATIVES

[75] Inventors: Jeffery B. Press, Rocky Hill; Zoltan Hajos, Princeton, both of N.J.

[73] Assignee: Ortho Pharmaceutical Corporation, Raritan, N.J.

[21] Appl. No.: 163,488

[22] Filed: Mar. 3, 1988

[51] Int. Cl.[4] ................. C07D 487/04; A61K 31/415
[52] U.S. Cl. .................................... 514/258; 544/256; 544/262
[58] Field of Search ................. 544/256, 262; 514/258

[56] References Cited

U.S. PATENT DOCUMENTS 4,460,586  7/1984  Berthold .............................. 424/250
4,603,203  7/1986  Furukawa et al. .................. 544/256
4,714,698 12/1987  Roch et al. ......................... 544/256

FOREIGN PATENT DOCUMENTS 2186573A  8/1987  United Kingdom .

Primary Examiner—Nicholas S. Rizzo
Attorney, Agent, or Firm—Benjamin F. Lambert

[57] ABSTRACT

4-Substituted pyrazolo[3,4-d]pyrimidine derivatives and a method of synthesis for the derivatives are described. The 4-substituted pyrazolopyrimidine derivatives are useful as cardiotonic agents and antiarryhythmic agents.

16 Claims, No Drawings

4-SUBSTITUTED PYRAZOLO[3,4-D]PYRIMIDINE DERIVATIVES

BACKGROUND OF THE INVENTION

1. Field of the Invention

The present application relates to compounds of the formula:

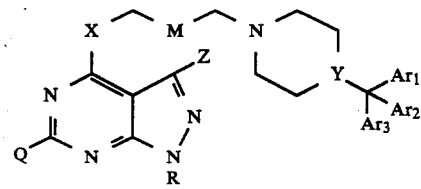

as further defined herein. The compounds possess intravenous and/or positive inotropic activity and are useful as cardiovascular agents. The compounds are especially useful as cardiotonic agents for improving cardiac ejection, particularly in the setting of acute or chronic heart failure. The compounds are also useful as antiarrhythmic agents for the treatment or prevention of cardiac arrythmias.

2. Description of the Prior Art

British patent application No. GB2186573 and German patent application No. DE3703633 relate to purine derivatives possessing cardiotonic and antiarrhythmic activity and having the following formula:

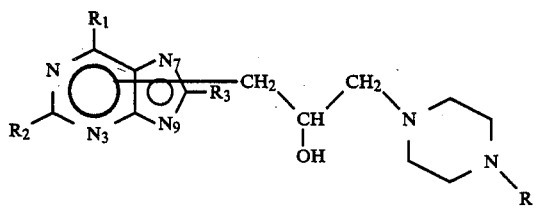

wherein R is an optionally substituted diphenylalkyl group. The side chain in the above formula is bonded to a ring nitrogen atom.

U.S. Pat. No. 4,460,586 relates to 3-aminopropoxyaryl derivatives of the formula:

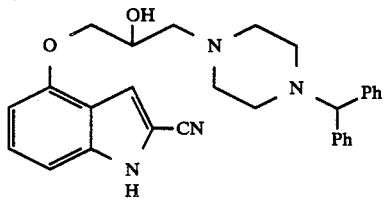

The compounds are useful as cardiotonic, antiarrhythmic and α- and β-adrenoceptor blocking agents. The U.S. patent is one of a series of patents that have issued claiming various 4-substituted indole derivatives.

SUMMARY OF THE INVENTION

The present invention is directed to 4-substituted pyrazolo[3,4-d]pyrimidine derivatives of the general formula:

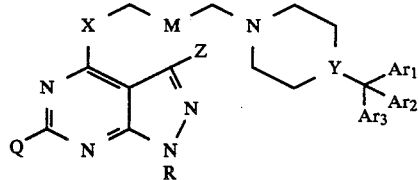

wherein X is S, O, NH and $NR_1$ wherein $R_1$ is $C_1$–$C_4$-lower alkyl;

M is $CH_2$, CHOH, $CHOCOR_2$ and $CHOR_2$ wherein $R_2$ is $C_1$–$C_8$- straight or branched chain lower alkyl, phenyl and substituted phenyl wherein the substituent on the phenyl ring is $C_1$–$C_4$- lower alkyl, $CF_3$, halo such as fluoro, chloro, bromo and iodo, $NO_2$, CN, $C_1$–$C_4$- lower alkyl, $C_1$–$C_4$- lower alkoxy, $NO_2$ and CN;

Y is nitrogen, $N(CH_2)_n$ wherein n is an integer from 0–4 or a carbon atom having a double bond (C=) attached to the carbon atom to which $Ar_1$, $Ar_2$ and $Ar_3$ are attached;

$Ar_1$, $Ar_2$ and $Ar_3$ are independently selected from H, $C_1$–$C_4$- lower alkyl, phenyl, substituted phenyl wherein the substituent is $C_1$–$C_4$-lower alkyl, $C_1$–$C_4$- lower alkoxy, $CF_3$, halo and perhalo such as fluoro, chloro, bromo and iodo, $NO_2$, CN; naphthyl, pyridyl and thienyl;

Z is H, CN, OH or $CO_2R_3$ wherein $R_3$ is H, $C_1$–$C_4$ lower alkyl and halo such as fluoro, bromo, chloro and iodo; phenyl or substituted phenyl wherein the substituent is $C_1$–$C_4$-lower alkyl, $NO_2$, halo such as chloro, bromo, iodo or fluoro, CN or $CF_3$;

R is H, $C_1$–$C_4$- lower alkyl, cyclopentyl, cyclohexyl, benzyl, $C_2$–$C_6$-lower alkenyl, $C_2$–$C_6$-lower alkynyl, tetrahydropyranyl and tetrahydrofuranyl;

Q is halo such as fluoro, bromo, chloro and iodo; amino, $C_1$–$C_4$-lower alkyl and OH.

Also included are the optically active isomers of the 4-substituted pyrazolopyrimidine derivatives.

In the above general formula at least one of $Ar_1$ $Ar_2$ and $Ar_3$ is an aromatic group and when Y is a carbon atom attached to a double bond (C=) only $Ar_1$ and $Ar_2$ are attached to the carbon atom.

The compounds of the general formula are useful as cardiovascular agents, and in particular as cardiotonic agents, and are also useful as antiarrhythmic agents

DETAILED DESCRIPTION OF THE INVENTION

The invention in its broadest aspects relates to 4-substituted pyrazolo[3,4-d]pyrimidinyl piperazine and piperidine derivatives which exhibit positive inotropic activity.

The compounds of the present invention wherein X is sulfur can be prepared as outlined in Scheme 1.

SCHEME 1

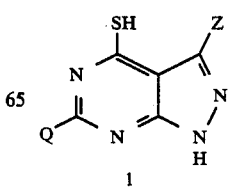

1

-continued
SCHEME 1

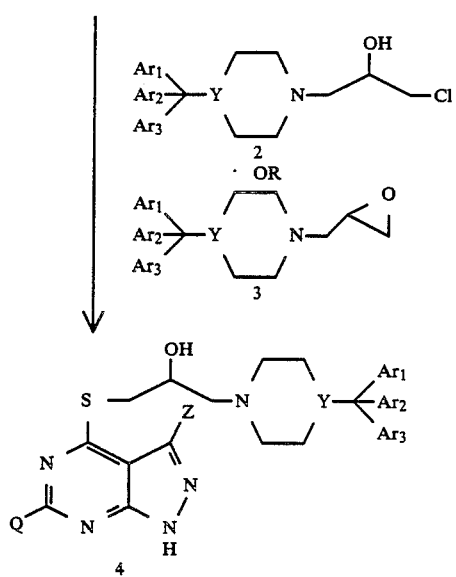

SCHEME 2

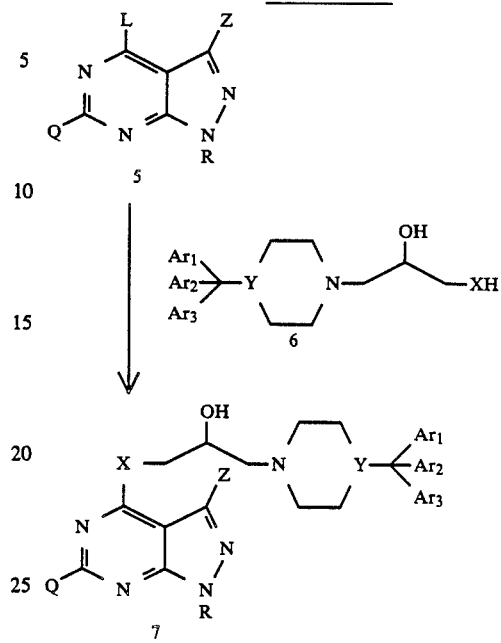

In this case, the appropriately substituted 4-mercaptopyrazolo[3,4-d]pyrimidine derivative 1 is treated with a base such as amines (for example, triethylamine), metal hydroxides (for example, sodium or potassium hydroxide), metal hydrides (for example, sodium hydride) in an inert solvent such as dimethylformamide (DMF) or tetrahydrofuran (THF). The anion so formed is reacted with appropriately substituted alkylating agents such as the chloride 2 or the epoxide 3 and the reactants are allowed to react for about 2 to 200 hours at a temperature of about 0° to 100° C. to form the compounds of the invention 4. The chlorides 2 and epoxides 3 used as the alkylating agents are either commercially available or they can be prepared by procedures found in the chemical literature and available to those skilled in the art.

Alternatively, the compounds of the present invention(7) wherein X is sulfur (S), NH, $NR_1$ or oxygen (O) can be prepared by the procedure outlined in Scheme 2. An appropriately substituted pyrazolo[3,4-d]pyrimidine 5 having a suitable leaving group (L) in the 4-position on the six membered ring is reacted with an appropriately substituted alcohol 6 where X is oxygen, with an amine where X is NH or $NR_1$, or with a mercaptan where X is sulfur, in a suitable solvent such as benzene, toluene, DMF, DMSO or THF, for example. As the leaving group (L) a chloro, bromo, mesyloxy or tosyloxy group may be employed. The pyrazolo[3,4-d]pyrimidine starting materials may or may not be substituted at the N-1 position. The reaction may be carried out in the presence of a base and/or a catalyst. Suitable bases which can be employed include alkali metal and alkaline earth metal hydroxides and hydrides such as sodium or potassium hydroxide, sodium or potassium hydride, and sodium or potassium metal. The reaction may also be carried out in the presence of a phase transfer or a crown ether catalyst such as 18-crown-6, for example. When the group at N-1 is a protecting group it can be removed by acid (in the case where $R_3$ is tetrahydropyranyl or tetrahydrofuranyl) or hydrogenolysis (in the case where $R_3$ is benzyl).

The compounds of the present invention can also be prepared as outlined in Scheme 3. An appropriately substituted alcohol 8 is reacted with an acid chloride, such as acetyl chloride or propionyl chloride, for example, or the corresponding acid anhydride in the presence of a base such as, for example, triethylamine or pyridine, in a suitable solvent such as THF or methylene chloride, for example, to form the ester derivative 9 ($R_4$ is $COR_2$ wherein $R_2$ is as defined above). If an alkyl iodide such as methyl iodide, for example, is employed as the alkylating agent, the reaction is generally carried out in the presence of a strong base such as sodium hydroxide or sodium hydride, for example, to form the ether derivative 10 ($R_4=R_2$ wherein $R_2$ is as defined above). In those cases where a protecting group such as tetrahydropyranyl, for example, is employed, the protecting group may be removed by hydrolysis with mild acid such as dilute hydrochloric acid.

The compounds of the present invention wherein X is sulfur can also be prepared as outlined in Scheme 4 where an appropriately substituted 4-pyrazolo[3,4-d]pyrimidine derivative 1 is treated with epichlorohydrin or glycidyl tosylate in either its racemic or optically active [(2R)-(−) or 2S-(+)] form in a suitable solvent, such as ethanol, acetonitrile, DMF or DMSO. The reaction is carried out at a temperature of about 0°–50° C. for a period of about several hours to about 10 days to give the chloride derivative 11. The reaction may optionally be carried out in the presence of a base such as sodium hydride. Treatment of the chloride derivative 11 with an appropriately substituted benzhydryl piperazine 12 either neat or in the presence of a solvent at a temperature of about 15°–50° C. for from about several hours to several weeks results in the pyrazolo[3,4-d]-pyrimidinyl piperazine derivative 13 in the racemic or optically active forms. Suitable solvents that can be employed in the reaction include methanol, ethanol, DMF and DMSO.

SCHEME 3

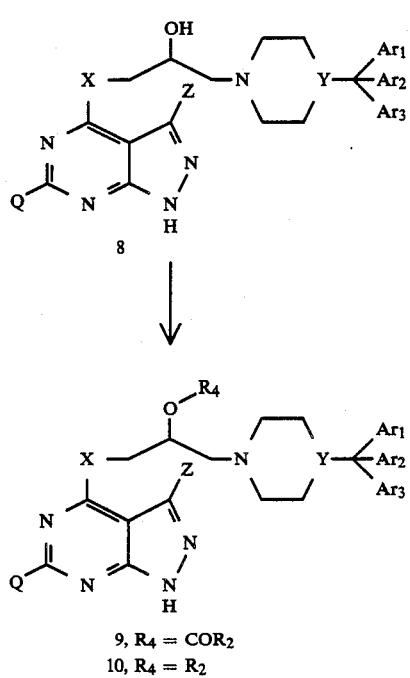

9, R₄ = COR₂
10, R₄ = R₂

SCHEME 4

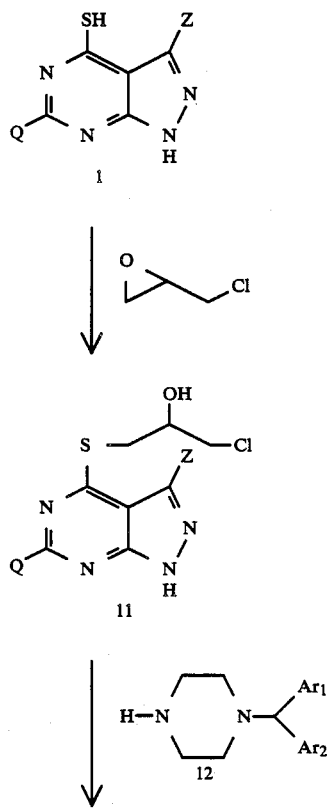

-continued
SCHEME 4

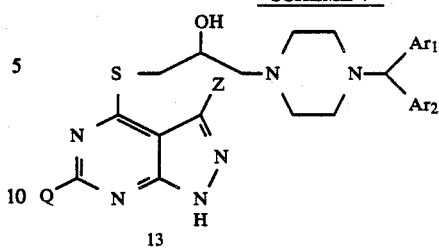

The benzhydryl piperazine compounds 12 are available commercially or they can be prepared according to literature procedures known to those skilled in the art. Unsymmetrical triaryl compounds may be prepared by reacting an aromatic carboxylic acid derivative such as ethyl 2-naphthalenecarboxylate with an organometallic reagent such as 2-pyridyl lithium under controlled conditions to give 2-naphthyl 2-pyridyl ketone. This in turn may be reacted with an organometallic reagent such as 2-thienyl lithium to give 1-(2-naphthyl)-1-(2-pyridyl)-1-(2-thienyl)methanol. This alcohol may in turn be reacted with halogenating agents such as thionyl chloride to give the corresponding chloromethane derivative in a manner similar to that described in Procedure 20. Reaction with piperazine in a like manner as described in Procedure 20 gives the requisite piperazine derivative. By varying the aromatic carboxylic acid derivative and the choice of the organometallic reagents in this procedure, a variety of tris- and bis-unsymmetrical benzhydryl piperazine derivatives may be prepared.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included; injectable suspensions may also be prepared, in which case appropriate liquid carriers, suspending agents and the like may be employed. The pharmaceutical compositions will generally contain a dosage unit, e.g., tablet, capsule, powder, injection, teaspoonful and the like, from about 0.01 to about 50 mg/kg, and preferably from about 0.1 to about 10 mg/kg of the active ingredient.

The following examples describe the invention in greater particularity and are intended to be a way of illustrating but not limiting the invention. Some of the compounds in the examples were obtained as the hydrate. The water can be removed from the hydrates by drying at temperatures below the melting point of the compound.

EXAMPLE 1

4-[1-[1-Bis(4-fluorophenyl)methyl]piperazin-4-yl]-2-hydroxy-3-propanylthio]-1H-pyrazolo[3,4-d]pyrimidine, Pentane (30 mL) was added to sodium hydride (0.28 g, 5.8 mmol, 50% suspension in mineral oil) under nitrogen. The pentane was decanted to remove the oil. Anhydrous DMF (12 mL) was added and the reaction mixture cooled to 0° C. 4-Mercapto-1H-pyrazolo [3,4-d]pyrimidine (0.76 g, 5 mmol) was added in small portions over a period of 10 min. 1-(1-Chloro-2-hydroxy-3-propanyl)-4-[bis(4-fluorophenyl)methyl]piperazine (2.0 g, 5.1 mmol) was added to the resultant light green solution, after an additional 10 min, in small portions over a period of 5 min at 0° C. After the addition was complete the reaction mixture was allowed to come to room temperature and was stirred under nitrogen for 6 days. The DMF was evaporated in vacuo (1 mm Hg) at 50° C. The residue was dispersed in methylene chloride and filtered through Celite. The filtrate was washed with water (2×50 mL), dried (sodium sulfate), filtered and evaporated in vacuo to give an oil (2.44 g). Flash chromatography over silica gel using 10% methanol/methylene chloride gave the purified product (0.84 g), which was re-flash chromatographed using 5% methanol/methylene chloride to give pure product (0.3 g, 15%), mp 88°–91° C. 100 MHz $^1$H NMR (CDCl$_3$) $\delta$: 8.70 (s, 1H), 8.14 (s, 1H), 7.29 (m, 4H), 6.95 (m, 4H), 4.21 (s, 1H), 4.10 (m, 1H), 3.50 (m, 2H), 2.6 (m, 2H), 2.5–2.6 (m, 8H). DCI/MS (M+1) 497.

Anal. Calcd. for C$_{25}$H$_{26}$F$_2$N$_6$OS: C, 60.46; H, 5.28; N, 16.92. Found: C, 60.76; H, 5.31; N, 16.33.

EXAMPLE 2

4-[2-Hydroxy-1-[(diphenylmethyl)piperazin-4-yl)-3-propanylthio]-1H-pyrazolo[3,4-d]pyrimidine Hemihydrate, Pentane (30 mL) was added to sodium hydride (0.28 g, 5.8 mmol, 50% suspension in mineral oil) and the mixture was stirred under nitrogen. The pentane was decanted. Anhydrous DMF (12 mL) was added and the suspension was cooled to 0° C. 4-Mercapto-1H-pyrazolo[3,4-d]pyrimidine (0.76 g, 5 mmol) was added in small portions over a period of 10 min. To 1-(1-Chloro-2-hydroxy-3-propanyl)-4-diphenylmethylpiperazine (1.72 g, 5 mmol) was added in small portions to the resultant light green solution at 0° C. over a period of 5 min. After the addition was complete, the mixture was allowed to warm to room temperature and was stirred under nitrogen for 48 h. The DMF was evaporated in vacuo (1 mm Hg) at 50° C. The residue was triturated in methylene chloride, and was filtered. The filtrate was washed with water (2×50 mL), dried (Na$_2$SO$_4$), filtered, and evaporated in vacuo to give a solid (1.83 g). Flash chromatography over silica gel using 10% methanol/methylene chloride gave the desired product (0.45 g, 25%) mp 78°–80° C. 100 MHz $^1$H NMR (CDCl$_3$) $\delta$: 8.71 (s, 1H), 7.2–7.4 (m, 10H), 4.22 (s, 1H), 4.11 (m, 1H), 3.55 (m, 2H), 2.6 (m, 2H), 2.5–2.6 (m, 8H). DCI/MS (M+1) 461.

Anal. Calcd. for C$_{25}$H$_{28}$N$_6$OS•½H$_2$O: C, 63.94; H, 6.23; N, 17.89. Found: C, 64.22; H, 6.40; N, 17.51.

EXAMPLE 3

4-[3-[4-[Bis(4-fluorophenyl)methyl]-piperazin-1-yl]-2-hydroxy-propoxy]-1-(tetrahydropyran-2-yl)pyrazolo[3,4-d]pyrimidine, A toluene solution (30 mL) of 3-[4-[bis(4-fluorophenyl)methyl]-1-piperazinyl]-1,2-propanediol (3.98 g, 11 mmol) was added dropwise to a stirred mixture of 4-chloro-1-(tetrahydropyran-2-yl)-pyrazolo[3,4-d]pyrimidine (2.387 g, 10 mmol), powdered KOH (0.485 g, 8.51 mmol), 18-crown-6 (3, 90.2 mg, 0.34 mmol) in toluene (70 mL) over a 20 min period. The mixture was stirred at room temperature for 3 h and washed with water (3×70 mL). The organic layer was dried (Na$_2$SO$_4$), filtered and evaporated to dryness. The oily residue (7.0 g) was purified on a medium pressure silica gel column eluting with increasing proportions of methanol in methylene chloride. The title compound was obtained as the major product (1.49 g, 41%), mp 101°–105° C. IR (KBr) cm$^{-1}$: 2466, 2446, 2401, 1603, 1568, 1506, 1347, 1222. $^1$H NMR (CDCl$_3$) $\delta$: 8.35 (s, 1H, 3 or 6-H), 8.12 (s, 1H, 3 or 6-H), 6.9–7.4 (m, 8H, Ar—H), 5.0 (m, 1H, N—O—CH—C), 4.6 (m, 2H, OCH$_2$), 4.23 [s, 1H, CH(O)$_2$], 4.15 (m, 2H, HCOH, O-CHN), 3.8 (m, 1H, OCNH), 1.6–2.9 (m, 16H, CH$_2$, NCH$_2$; MS(DCI): 565 (MH)+.

Anal. Calcd. for C$_{30}$H$_{34}$F$_2$N$_6$O$_3$: C, 63.82; H, 6.07; N, 14.88. Found: C, 63.49; H, 6.04; N, 15.06.

EXAMPLE 4

4-[1-[1-[Bis(4-chlorophenyl)methyl]piperazin-4-yl]-2-hydroxy-3-propanylthio]-1H-pyrazolo[3,4-d]pyrimidine Pentane (30 mL) was added to sodium hydride (0.28 g, 5.8 mmol of 50% suspension in mineral oil) and the mixture was stirred under nitrogen. The pentane was decanted. Anhydrous DMF (6.0 mL) was added and the suspension was cooled to 0° C. 4-Mercapto-1H-pyrazolo[3,4-d]pyrimidine (0.76 g, 5 mmol) was added in small portions over a period of 10 min. 1-(1-Chloro-2-hydroxy-3-propanyl)-4-[bis(4-chlorophenyl)piperazine (1.8 g, 4.35 mmol) dissolved in anhydrous DMF (12 mL) was added to the resultant light green solution over a period of 5 min. After the addition was complete, the mixture was warmed to room temperature and stirred for 72 h. The DMF was evaporated in vacuo (1 mm Hg) at 50° C. The residue was triturated in methylene chloride (50 mL) and filtered. The filtrate was washed with water (25 mL), dried (Na$_2$SO$_4$), filtered, and evaporated in vacuo to give oil (2.7 g).

Flash chromatography using 10% methanol/methylene chloride gave the named product (380 mg, 20%), mp 115°–118° C. 300 MHz $^1$H NMR (CDCl$_3$) $\delta$: 8.70 (s, 1H), 8.14 (s, 1H), 7.27 (m, 8H), 4.18 (s, 1H), 4.10 (m, 1 h), 3.50 (m, 2H), 2.4–2.6 (m, 10H). DCI/MS: 529/531.

Anal. Calcd. for C$_{25}$H$_{26}$Cl$_2$N$_6$OS: C, 56.71; H, 4.96; N, 15.87. Found: C, 56.79; H, 5.01; N, 14.99.

EXAMPLE 5

1-(1,2-Epoxy-3-propanyl)-4-[1-(diphenylmethylpiperazin-4-yl]-2-hydroxy-3-propanylthio]-1H-pyrazolo[3,4-d]pyrimidine Triethylamine (0.7 mL, 5 mmol) and 1-(1-chloro-2-hydroxy-3-propanyl)-4-(diphenylmethyl)piperazine (1.72 g, 5 mmol) was added to 4-mercapto-1H-pyrazolo[3,4-d]pyrimidine (0.78 g, 5 mmol) in DMF (10 mL) in portions over a 5 min period. The solution was stirred under nitrogen for 4 days and DMF was removed under vacuum (50° C., 0.5 mmHg). The residue was dissolved in methylene chloride and the solution was washed with water (1×100 mL), saturated brine (1×100 mL) and the organic layer was filtered through celite and evaporated to give a foam (1.47 g). The crude material was eluted through silica gel using 10% methanol: methylene chloride which was extracted with methylene chloride and the organic layer was dried over $Na_2SO_4$ and evaporated and dried in vacuo to give the title compound, 0.36 g (13.9%), mp 87°-92° C. 400 MHz $^1$H NMR (CDCl$_3$) δ: 8.70 (s, 1H), 8.1 (s, 1H), 7.4 (m, 5H), 7.15 (m, 5H), 4.25 (s, 1H), 4.11 (m, 1H), 3.55 (m, 2H), 3.7–2.4 (m, 15H). DCI/MS (M+1) 517.

Anal. Calcd. for $C_{28}H_{32}N_6O_2S$: C, 65.09; H, 6.24; N, 16.27; S, 6.21. Found: C, 65.59; H, 6.47; N, 16.42; S, 6.18.

EXAMPLE 6

(2S)-(+)-4-[1-Bis(4-fluorophenyl)methyl]piperazin-yl]-2-hydroxy-3-propanylthio]-1H-pyrazolo[3,4-d]pyrimidine Using a procedure analogous to that described in Example 1, 4-mercapto-1H-pyrazolo[3,4-d]pyrimidine (1.52 g, 10.0 mmol), sodium hydride (0.50 g, 10 mmol) and (2S)-(−)-(1,2-epoxypropyl)-4-[bis(4-fluorophenyl)methyl]piperazine (3.3 g, 9.6 mmol) were reacted for 72 h in DMF (25 mL total volume). Workup and purification gave the title compound, 0.8 g (25%) as a light beige solid, mp 102°-105° C., $[\alpha]_D^{22}$ +5.7° (5% EtOH).

Anal Calcd. for $C_{25}H_{26}F_2N_6OS$: C, 60.46; H, 5.28; N, 16.92. Found: C, 60.67; H, 5.48; N, 16.29.

EXAMPLE 7

CARDIOTONIC ACTIVITY

Adult mongrel dogs were anesthetized with sodium pentobarbital (45 mg/kg, i.p.) and artificially respired. Mean arterial pressure (MAP) was recorded from a cannulated femoral artery and drugs were infused into a cannulated femoral vein. The arterial pressure pulse was used to trigger a cardiotachometer for determination of heart rate (HR). Left ventricular pressure was measured with a Millar catheter and dP/dt$_{max}$ was derived. A right thoracotomy was performed and myocardial contractile force (CF) was measured with a Walton Brodie strain gauge sutured to the right ventricle. The ventricular muscle was stretched to produce a baseline tension of 100 g. A standard dose of dopamine (10–15 ug/kg/min for 3 min) was administered to determine myocardial responsiveness to inotropic stimulation. Test compounds were solubilized in a small volume of DMF diluted to a final concentration of 10% in physiological saline. Alternatively, where possible, a soluble hydrochloride salt was prepared by addition of 0.1 N HCl diluted in physiological saline. Vehicles were tested in appropriate volumes and found to exert less than a 5% effect on contractile force. For iv studies, compounds were administered by infusion pump (one drug per animal) at rates of 0.58–2.2 mL/min in three to four stepwise increasing doses. Each dose was infused over 5 min immediately after the effect of the previous dose peaked. MAP, HR, dP/dt$_{max}$ and CF responses were continuously monitored on a Beckman or Gould recorder and expressed as a percent change from pre-drug control values vs. the cumulative dose of drug administered. For these studies, n represents the number of test animals used.

Quantitation of the inotropic potency was obtained by calculation of the contractile force (CF) ED$_{50}$. This was defined as the dose of compound that produced a 50% increase above baseline in myocardial contractile force. The value was obtained from three to four point dose-response curves using either graphical estimation (n<3) or linear regression analysis (n≧3). Data from this evaluation is shown in Table 1. Numbers in parentheses are number of animals screened.

TABLE 1

Cardiovascular activity of compounds of the Invention.

| Example | Dose (mg/kg) | n | MAP | HR | dP/dt | CF |
|---------|--------------|---|-----|----|----|-----|
| 1 | 1.875 (ED50 = 225 ug/kg) | 2 | −3 | −10 | 124 | 205 |
| 2 | 1.875 | 1 | −12 | −11 | 48 | 97 |
| 3 | 1.875 | 1 | −13 | 1 | 1 | 14 |
| 4 | 1.875 (ED50 = 450 ug/kg) | 2 | 8 | 1 | 90 | 163 |
| 5 | 1.875 | 1 | −8 | −14 | 28 | 38 |

PROCEDURE 1

1-(1-Chloro-2-hydroxy-3-propanyl)-4-[bis(4-fluorophenyl)methyl]piperazine Monohydrate

[Bis(4-fluorophenyl)methyl]piperazine, (14.4 g, 0.05 mol) in ethanol (200 mL) was added dropwise to epichlorohydrin (3.5 mL, 0.05 mol) in ethanol (12 mL) at 0° C. with NaHCO$_3$ anhydrous (4.2 g, 0.05 mol) over 45 min under N$_2$. The ice bath was removed and the mixture was allowed to come to room temperature. After 18 h the NaHCO$_3$ was removed by filtration via a sintered glass funnel and the ethanol in the filtrate was removed in vacuo to give the crude product (21.3 g). Flash chromatography over silica gel using 2.0% methanol: methylene chloride gave pure product (10.05 g, 52.9%) as an amber oil. DCI/MS (M+1) 381. 400 MHz $^1$H NMR (CDCl$_3$) δ: 7.3 (m, 4H), 6.95 (m, 4H), 4.2 (s, 1H), 3.95 (m, 1H), 3.55 (m, 2H), 2.7 (m, 2H), 2.5 (m, 4H), 2.4 (m, 4H).

Anal. Calcd. for $C_{20}H_{23}ClF_2N_2O\cdot H_2O$: C, 60.22; H, 6.32; N, 7.02. Found: C, 60.29; H, 6.21; N, 6.83.

PROCEDURE 2

1-(1-Chloro-2-hydroxy-3-propanyl)-4-(diphenylmethyl)piperazine

Diphenylmethylpiperazine (16.4 g, 0.065 mol) in ethanol (250 mL) was added dropwise to epichlorohydrin (5.1 mL, 0.065 mL) in ethanol (13 mL) with anhydrous NaHCO$_3$ (0.065 mol, 5,46 g) at 0° C., over 45 min at room temperature under N$_2$. After 17 h the NaHCO$_3$ was removed by filtration via a sintered glass funnel and the ethanol removed from the filtrate in vacuo giving a white-yellow solid (21.5 g). This solid after triturating with Et$_2$O (300 mL) gave a precipitate which was filtered and dried in vacuo to give the pure product (5.11 g, 22.8%) mp 114°–116° C. DCI/MS (M+1) 345. 400 MHz $^1$H NMR (CDCl$_3$) δ: 7.2–7.4 (m, 10H), 4.2 (s, 1H), 3.9 (m, 1H), 3.55–3.7 (m, 2H), 2.7 (m, 2H), 2.45 (m, 8H).

Anal. Calcd. for C$_{20}$H$_{25}$ClN$_2$O: C, 69.60; H, 7.20; N, 8.10. Found: C, 69.59; H, 7.44; N, 7.96.

PROCEDURE 3

1-(1-Chloro-2-hydroxy-3-propanyl)-4-benzylpiperazine

1-Benzylpiperazine (8.66 mL, 50 mmol) in EtOH (100 mL) was added dropwise to epichlorohydrin (3.92 mL, 50 mmol) in EtOH (25 mL) with NaHCO$_3$ (4.2 g, 50 mmol) over 30 min at 0° C. under nitrogen. After 16 h the EtOH was removed in vacuo and the crude product eluted through silica gel (5% methanol: methylene chloride) to give pure product (10.12 g, 75.3%) as an amber oil. DCI/MS (M+1) 269. 400 MHz $^1$H NMR (CDCl$_3$) δ: 7.3 (m, 5H), 4.95 (m, 1H), 4.5 & 4.6 (m, 2H), 3.95 (m, 1H), 3.6 (m, 2H), 3.5 (s, 2H), 2.7 (m, 4H), 2.4 (m, 4H).

Anal. Calcd. for C$_{14}$H$_{21}$ClN$_2$O: C, 62.50; H, 7.87; N, 10.40. Found: C, 62.41; H, 7.83; H, 10.35.

PROCEDURE 4

1-(1-Chloro-2-hydroxy-3-propanyl)-4-piperonylpiperazine

1-Piperonylpiperazine (11.0 g, 50 mmol) in EtOH (125 mL) was added dropwise to epichlorohydrin (3.9 mL, 50 mmol) in EtOH (25 mL) and NaHCO$_3$ (4.2 g, 50 mmol) over 45 min at 0° C., under nitrogen. After 16 h and removal of the EtOH in vacuo, the crude material was passed through silica gel (vacuum, 5% methanol: methylene chloride) to give pure product (3.85 g, 26.4%) as an amber oil. DCI/MS (M+1) 313. 400 MHz $^1$H NMR (CDCl$_3$) δ: 7.25 (s, 1H), 6.7–6.8 (m, 2H), 5.9 (s, 2H), 4.6 (m, 1H), 3.9 (m, 1H), 3.5 (m, 2H), 3.4 (s, 2H), 2.4–2.7 (m, 10H).

Anal. Calcd. for C$_{15}$H$_{21}$ClN$_2$O$_3$: C, 57.59; H, 6.77; N, 8.95. Found: C, 57.24; H, 6.84; N, 8.73.

PROCEDURE 5

1-(1-Chloro-2-hydroxy-3-propanyl)-4-(4-chlorobenzhydryl)piperazine Hemihydrate 4-Chlorobenzhydrylpiperazine (14.34 g, 50 mmol) in EtOH (150 mL) was added to epichlorohydrin (3.92 mL, 50 mmol) in ethanol (25 mL) and NaHCO$_3$ (4.2 g, 50 mmol) over 45 min at 0° C. under nitrogen. After 20 h, the EtOH was removed in vacuo and the residue eluted through silica gel using 50% methanol: methylene chloride to give the pure product (3.40 g, 18.3%) as a white solid, mp 72°–74° C. DCI/MS (M+1) 379. 400 MHz $^1$H NMR (CDCl$_3$) δ: 7.5–7.35 (m, 9H), 4.2 (s, 1H), 3.65 (m, 2H), 2.9 (m, 2H), 2.7–2.6 (m, 8H).

Anal. Calcd. for C$_{20}$H$_{24}$Cl$_2$N$_2$O•½H$_2$O: C, 61.80; H, 6.44; N, 7.20. Found: C, 61.67; H, 6.37; N, 7.10.

PROCEDURE 6

Bis(4-chlorophenyl)chloromethane

Thionyl chloride (10 mL, 137 mmol) was added dropwise to 4-chlorobenzhydrol (12.66 g, 50 mmol) in CH$_2$Cl$_2$ (200 mL) under nitrogen over 15 min. After 18 h and solvent removal in vacuo, the crude product was dissolved in methylene chloride (250 mL) and washed with saturated NaHCO$_3$ (3×50 mL), dried over Na$_2$SO$_4$, and concentrated in vacuo to a thin, amber oil (12.53 g). Upon standing at room temperature for 1 h, crystallization occured to give pure product (12.5 g, 88.4%) as a white solid, mp 61°–64° C. DCI/MS (M+1) 235. 400 MHz $^1$H NMR (CDCl$_3$) δ: 7.35 (m, 8H), 6.05 (s, 1H).

Anal. Calcd. for C$_{13}$H$_9$Cl$_3$: C, 57.49; H, 3.34. Found: C, 57.69; H, 3.46.

This is a known compound *Chem. Abstract.*, 1957, 51, 9717a.

PROCEDURE 7

1-(1-Chloro-3-propanyl)-4-[bis(4-fluorophenyl)methyl]piperazine

Pentane (50 mL) was added to sodium hydride (0.50 g, 11 mmol of 50% suspension in mineral oil) and the mixture was stirred under nitrogen. The pentane was decanted. Anhydrous DMF (12 mL) was added and the suspension was cooled to 0° C. [Bis(4-fluorophenyl)methylpiperazine (2.9 g, 10 mmol) was added in anhydrous DMF (14 mL) at 0° C. within 10 min. The reaction mixture was allowed to warm to room temperature. After 1 h, the mixture was cooled to 0° C. and 1-chloro-3-bromopropane (5 mL, 50 mmol) in anhydrous DMF (5 mL) was added to the light green solution over a period of 10 min. The mixture was stirred under nitrogen at room temperature for 72 h. The solvents were evaporated in vacuo (1 mm Hg) at 50° C. The residue was triturated in methylene chloride and filtered through Celite. The filtrate was washed with water (2×100 mL), dried (sodium sulfate), filtered, and the filtrate evaporated in vacuo to give crude chloropropyl compound (3.65 g). Pentane (50 mL) was added, and on the next day the pentane insoluble solid was filtered. The filtrate was evaporated in vacuo to give title compound (2.3 g, 75%) as a clear, colorless oil. 100 MHz $^1$H MR (CDCl$_3$) δ: 7.32 (m, 4H), 6.95 (m, 4H), 4.2 (s, 1H), 3.57 (m, 2H), 2.2–2.6 (m, 10H), 1.9 (m, 2H). DCI/MS (M+1) 361.

Anal. Calcd. for C$_{20}$H$_{23}$ClF$_2$N$_2$: C, 65.83; H, 6.35; N, 7.68.

Found: C, 65.59; H, 6.42; N, 7.63.

PROCEDURE 8

3-[4-[Bis(4-fluorophenyl)methyl]-1-piperazinyl]-1,2-propanediol 0.25 hydrate A solution of glycidol (1.63 g, 22 mmol) in MeOH (25 mL) was slowly added to a stirred and warmed solution of 4-fluorobenzhydrylpiperazine (6.343 g, 22 mmol) in methanol (75 mL) under nitrogen. The mixture was stirred at room temperature for 18 h, refluxed for 2 h and evaporated to dryness. Methylene chloride was added to the syrupy residue and the solution was evaporated to dryness. The syrupy residue was purified by chromatography on a silica gel column (medium pressure). Elution with 2%–5% methanol in methylene chloride gave the title compound as a colorless syrup which upon prolonged evacuation formed a hygroscopic foam (5.84 g, 73%), mp 40°–50° C. IR(KBr) cm$^{-1}$: 3625, 3575; $^1$H NMR (CDCl$_3$) δ: 6.9–7.4 (m, 8H, Ar-H); 4.21 [s, 1H, CH(O)$_2$], 3.80 (m, 1H, HCOH), 3.73 and 3.49 (each m, each 1H, HOCH$_2$), 3.8–2.3 (m, 10H, N—CH$_2$); MS(DCI):363 (MH)+.

Anal. Calcd. for C$_{20}$H$_{24}$F$_2$N$_2$O$_2$•¼H$_2$O: C, 65.46; H, 6.73; N, 7.63.

Found: C, 65.09; H, 6.66; N, 7.49.

PROCEDURE 9

3-[4-(Diphenylmethyl)-1-piperazinyl]-1,2-propanediol

In a procedure analogous to that described above, 4-benzyhydrylpiperazine (12.61 g, 0.05 mmol) in MeOH (50 mL) was reacted with glycidol (3.704 g, 0.05 mmol) in methanol (20 mL) and worked up to give the title compound as a colorless crystalline solid, 13.20 g (81%), mp 130°-131° C. (mp 125°-126° C. reported by M. Verderame, *J. Med. Chem.*, 11, 1090 (1968)).

Anal. Calcd for $C_{20}H_{26}N_2O_2$: C, 73.59; H, 8.03; N, 8.58.

Found: C, 73.32; H, 8.21; N, 8.48.

PROCEDURE 10

3-[4-[Bis(4-fluorophenyl)methyl]-1-piperazinyl]-1,2-propanediol 0.25 Hydrate To a stirred and warmed solution of 4-fluorobenzhydrylpiperazine (6.343 g, 22 mmol) in MeOH (75 mL), a solution of glycidol (1.63 g, 22 mmol) in MeOH (25 mL) was added slowly under nitrogen. The mixture was stirred at room temperature for 18 h, refluxed for 2 h and evaporated to dryness. $CH_2Cl_2$ (4×100 mL) was added to the syrupy residue and the mixture was evaporated to dryness. The syrupy residue was purified by chromatography on a silica gel column (medium pressure). Eluting with 2%-5% MeOH/$CH_2Cl_2$ gave the title compound as a colorless syrup which upon prolonged evacuation formed a hygroscopic foam (5.84 g, 73%), mp 40°-50° C. IR(KBr) cm$^{-1}$: 3625, 3575; $^1$H NMR (CDCl$_3$) δ: 6.9-7.4 (m, 8H, Ar-H); 4.21 [s, 1H, CH(O)$_2$], 3.80 (m, 1H, HCOH), 3.73 and 3.49 (each m, each 1H, HOCH$_2$), 3.8-2.3 (m, 10H, N—CH$_2$); MS(DCI):363 (MH)+.

Anal. Calcd. for $C_{20}H_{24}F_2N_2O_2 \cdot \frac{1}{4}H_2O$: C, 65.46; H, 6.73; N, 7.63.

Found: C, 65.09; H, 6.66; N, 7.49.

PROCEDURE 11

3-[4-(Diphenylmethyl)-1-piperazinyl]-1,2-propanediol

In a procedure analogous to that of Procedure 1 above, 4-benzyhydrylpiperazine (12.61 g, 0.05 mmol) in MeOH (50 mL) was reacted with glycidol (3.704 g, 0.05 mmol) in MeOH (20 mL) and worked up to give the title compound as a colorless crystalline solid, 13.20 g (81%), mp 130°-131° C. (mp 125°-126° C. reported by M. Verderame, *J. Med. Chem.*, 11, 1090 (1968)).

Anal. Calcd. for $C_{20}H_{26}N_2O_2$: C, 73.59; H, 8.03; N, 8.58.

Found: C, 73.32; H, 8.21; N, 8.48.

PROCEDURE 12

1-(1-Chloro-2-hydroxy-3-propanyl)-4-[bis(4-fluorophenyl)-methyl]piperazine Monohydrate To a mixture of epichlorohydrin (3.5 mL, 0.05 mol) in ethanol (12 mL) at 0° C. (ice bath) and anhydrous NaHCO$_3$ (4.2 g, 0.05 mol), [bis(4-fluorophenyl)methyl]piperazine (14.4 g, 0.05 mol) in ethanol (200 mL) was added dropwise over 45 min under N$_2$. The ice bath was removed and the mixture was allowed to come to room temperature. After 18 h the NaHCO$_3$ was removed by filtration via a sintered glass funnel and the ethanol in the filtrate was removed in vacuo to give the crude product (21.3 g). Silica gel flash chromatography using 2.0% MeOH:CH$_2$Cl$_2$ gave pure product (10.05 g, 52.9%) as an amber oil. DCI/MS (M+1) 381. 400 MHz $^1$H NMR (CDCl$_3$) δ: 7.3 (m, 4H), 6.95 (m, 4H), 4.2 (s, 1H), 3.95 (m, 1H), 3.55 (m, 2H), 2.7 (m, 2H), 2.5 (m, 4H), 2.4 (m, 4H).

Anal. Calcd. for $C_{20}H_{23}ClF_2N_2O \cdot H_2O$: C, 60.22; H, 6.32; N, 7.02.

Found: C, 6.29; H, 6.21; N, 6.83.

PROCEDURE 13

1-(1-Chloro-2-hydroxy-3-propanyl)-4-(diphenylmethyl)piperazine

To a mixture of epichlorohydrin (5.1 mL, 0.065 mL) in ethanol (13 mL) and anhydrous NaHCO$_3$ (0.065 mol, 5.46 g) at 0° C., diphenylmethylpiperazine (16.4 g, 0.065 mol) in ethanol (250 mL) was added dropwise over 45 min at room temperature under N$_2$. After 17 h the NaHCO$_3$ was removed by filtration via a sintered glass funnel and the ethanol was removed from the filtrate in vacuo giving a white-yellow solid (21.5 g). This solid after trituration with Et$_2$O (300 mL) gave a precipitate which was filtered and dried in vacuo to give the pure product (5.11 g, 22.8%) mp 114°-116° C. DCI/MS (M+1) 345. 400 MHz $^1$H NMR (CDCl$_3$) δ: 7.2-7.4 (m, 10H), 4.2 (s, 1H), 3.9 (m, 1H), 3.55-3.7 (m, 2H), 2.7 (m, 2H), 2.45 (m, 8H).

Anal. Calcd. for $C_{20}H_{25}ClN_2O$: C, 69.60; H, 7.20; N, 8.10.

Found: C, 69.59; H, 7.44; N, 7.96.

PROCEDURE 14

1-(1-Chloro-2-hydroxy-3-propanyl)-4-benzylpiperazine

To a mixture of epichlorohydrin (3.92 mL, 50 mmol) in EtOH (25 mL) and anhydrous NaHCO$_3$ (4.2 g, 50 mmol) 1-benzylpiperazine (8.66 mL, 50 mmol) in EtOH (100 mL) was added dropwise over 30 min at 0° C. under nitrogen. After 16 h the EtOH was removed in vacuo and the crude product was eluted through silica gel (5% MeOH:CH$_2$Cl$_2$) to give pure product (10.12 g, 75.3%) as an amber oil. DCI/MS (M+1) 269. 400 MHz $^1$H NMR (CDCl$_3$) δ: 7.3 (m, 5H), 4.95 (m, 1H), 4.5 & 4.6 (m, 2H), 3.95 (m, 1H), 3.6 (m, 2H), 3.5 (s, 2H), 2.7 (m, 4H), 2.4 (m, 4H).

Anal. Calcd. for $C_{14}H_{21}ClN_2O$: C, 62.50; H, 7.87; N, 10.40.

Found: C, 62.41; H, 7.83; H, 10.35.

PROCEDURE 15

1-(1-Chloro-2-hydroxy-3-propanyl)-4-piperonylpiperazine

To a mixture of epichlorohydrin (3.9 mL, 50 mmol) in EtOH (25 mL) and anhydrous NaHCO$_3$ (4.2 g, 50 mmol), 1-piperonylpiperazine (11.0 g, 50 mmol) in EtOH (125 mL) was added dropwise over 45 min at 0° C., under nitrogen. After 16 h and removal of the EtOH in vacuo, the crude material was passed through silica gel (vacuum, 5% MeOH:CH$_2$Cl$_2$) to give pure product (3.85 g, 26.4%) as an amber oil. DCI/MS (M+1) 313. 400 MHz $^1$H NMR (CDCl$_3$) δ: 7.25 (s, 1H), 6.7-6.8 (m, 2H), 5.9 (s, 2H), 4.6 (m, 1H), 3.9 (m, 1H), 3.5 (m, 2H), 3.4 (s, 2H), 2.4-2.7 (m, 10H).

Anal. Calcd. for $C_{15}H_{21}N_2O_3Cl$: C, 57.59; H, 6.77; N, 8.95.

Found: C, 57.24; H, 6.84; N, 8.73.

PROCEDURE 16

1-(1-Chloro-2-hydroxy-3-propanyl)-4-(4-chlorobenzhydryl)piperazine Hemihydrate To a mixture of epichlorohydrin (3.92 mL, 50 mmol) in ethanol (25 mL) and NaHCO$_3$ (4.2 g, 50 mmol) 4-chlorobenzhydryl piperazine (14.34 g, 50 mmol) in EtOH (150 mL) was added dropwise over 45 min at 0° C. under nitrogen. After 20 h, the EtOH was removed in vacuo and the residue was eluted through silica gel using 50% MeOH:CH$_2$Cl$_2$ to give the pure product (3.40 g, 18.3%) as a white solid, mp 72°–74° C. DCI/MS (M+1) 379; 400 MHz $^1$H NMR (CDCl$_3$) δ: 7.5–7.35 (m, 9H), 4.2 (s, 1H), 3.65 (m, 2H), 2.9 (m, 2H), 2.7–2.6 (m, 8H).

Anal. Calcd. for C$_{20}$H$_{24}$Cl$_2$N$_2$O•½H$_2$O: C, 61.80; H, 6.44; N, 7.20.

Found: C, 61.67; H, 6.37; N, 7.10.

PROCEDURE 17

1-(1-Chloro-2-hydroxy-3-propanyl)-4-[bis(4-chlorophenyl)methyl]piperazine 4,4'-Dichlorobenzhydrylpiperazine ((6.0 g, 18.7 mmol) was reacted as above with epichlorohydrin to give the title compound as an amber oil, 3.67 g (49.8%). 100 MHz $^1$H NMR (CDCl$_3$) δ: 7.3 (s, 8H), 4.2 (s, 1H), 3.9 (m, 1H), 3.6 (d, 2H, J=10 Hz), 2.9 (m, 2H), 2.7–2.4 (m, 10H).

PROCEDURE 18

1-(1-Chloro-2-hydroxy-3-propoxy)-4-carbethoxypiperazine•Hemihydrate

Carbethoxypiperazine (7.28 mL, 50 mmol) was reacted as above with epichlorohydrin to give the title compound as a clear oil, 8.69 g (69.3%). DCI/MS (M+1) 251; 400 MHz $^1$H NMR (CDCl$_3$) δ: 4.15 (q, 2H, J=7.1 Hz), 3.9 (m, 1H), 3.6 (m, 2H), 3.5 (m, 4H), 2.6–2.4 (m, 4H), 2.5 (d, 2H, J=6.5 Hz), 1.25 (t, 3H, J=7.11 Hz).

Anal. Calcd. for C$_{10}$H$_{19}$ClN$_2$O$_3$•½H$_2$O: C, 46.24; H, 7.76; N, 10.78.

Found: C, 46.58; H, 7.47; N, 10.65.

PROCEDURE 19

1-(1-Chloro-2-hydroxy-3-propanyl)-4-(triphenylmethyl)piperazine•¼ Hydrate 1-(Triphenylmethyl)piperazine (5.25 g, 16 mmol) was reacted as above with epichlorohydrin to give the title compound as a white solid, 2.79 g (41.4%), mp 91°–94° C. DCI/MS (M+1) 421; 400 MHz $^1$H NMR (CDCl$_3$) δ: 7.5–7.15 (m, 15H), 3.86 (m, 1H), 3.52 (d, 2H, J=4.85 Hz), 2.9 (m, 2H), 2.8–2.4 (m, 10H).

Anal. Calcd. for C$_{26}$H$_{29}$ClN$_2$O•¼H$_2$O: C, 73.39; H, 6.99; N, 6.58.

Found: C, 73.34; H, 6.83; N, 6.53.

PROCEDURE 20

1-[Bis(4-chlorophenyl)methyl]piperazine

To 4-chlorobenzhydrol (12.66 g, 50 mmol) in CH$_2$Cl$_2$ (200 mL) under nitrogen, thionyl chloride (10 mL, 137 mmol) was added dropwise over 15 min. After 18 h and removal of the solvent in vacuo, the crude product was dissolved in CH$_2$Cl$_2$ (100 mL) and washed with saturated NaHCO$_3$ (3×), dried over Na$_2$SO$_4$, and concentrated in vacuo to a thin, amber oil (12.53 g). Upon standing at room temperature for 1 h, crystallization occured to give pure product (12.5 g, 88.4%) as a white solid, mp 61°–64° C. DCI/MS (M+1) 235. 400 MHz $^1$H NMR (CDCl$_3$) δ: 7.35 (m, 8H), 6.05 (s, 1H).

Anal. Calcd. for C$_{13}$H$_9$Cl$_3$: C, 57.49; H, 3.34.

Found: C, 57.69; H, 3.46.

This is a known compound: Chem. Abstract., 1957, 51, 9717a.

To piperazine (9.15 g, 106 mmol) in CHCl$_3$ (200 mL) containing potassium iodide (2.66 g, 16 mmol) under a nitrogen atmosphere, bis(4-chlorophenyl)chloromethane (9.5 g, 35 mmol) in CHCl$_3$ (100 mL) was added dropwise with stirring over a period of 45 min. After 6 days, the reaction mixture was filtered, concentrated and the crude product was purified by flash chromatography using 10% MeOH in CH$_2$Cl$_2$ to give the title compound as a thick amber oil. 400 MHz $^1$H NMR (CDCl$_3$) δ: 7.25 (m, 8H), 4.25 (s, 1H), 2.9 (m, 4H), 2.3 (m, 4H).

PROCEDURE 21

(2S)-(−)-(1,2-Epoxypropyl)-4-[bis(4-fluorophenyl)methyl]piperazine•¼ Hydrate To NaH (0.9 g, 18.75 mmol, 50% suspension in mineral oil) previously washed with pentane in DMF (8 mL) 4,4'-difluorobenzhydrylpiperazine (5.0 g, 17.4 mmol) in DMF (15 mL) was added dropwise under nitrogen over 15 min at 0° C. After 15 min at 0° C., the mixture was warmed to room temperature. After 2 h the mixture was cooled to 0° C., (2R)-(−)-glycidyl tosylate (4.0 g, 17.5 mmol) in DMF (16 mL) was added dropwise and the mixture was stirred at room temperature for 24 h under nitrogen. After filtration through celite, the mixture was concentrated in vacuo (1 mmHg, 55° C.) and the residue was dissolved in CH$_2$Cl$_2$. Refiltration of the solution, concentration and flash chromatography of the resultant oil through silica gel using 10% MeOH: CH$_2$Cl$_2$ gave the title compound as an amber oil, 4.66 g (82.6%); DCI/MS (M+1) 345; 400 MHz $^1$H NMR (CDCl$_3$) δ: 7.4 (m, 4H), 7.0 (m, 4H), 4.25 (s, 1H), 3.1 (m, 1H), 2.8 (m, 2H), 2.7–2.4 (m, 8H), 2.3 (m, 2H); [α]$_D^{22}$ −7.5° (5% in EtOH).

Anal. Calc'd for C$_{20}$H$_{22}$F$_2$N$_2$O•¼H$_2$O: C, 68.89; H, 6.50; N, 8.03.

Found: C, 69.17; H, 6.53; N, 8.02.

PROCEDURE 22

(2R)-(+)-(1,2-Epoxypropyl)-4-[bis(4-fluorophenyl)methyl]piperazine Hydrate

Using a similar procedure to that described above, (2S)-(+)-glycidyl tosylate (2.0 g, 8.76 mmol) was used to prepare the title compound as an amber oil, 2.57 g (77.8%); DCI/MS (M+1) 345; 400 MHz $^1$H NMR (CDCl$_3$) δ: 7.35 (m, 4H), 6.95 (m, 4H), 4.2 (s, 1H), 3.1 (m, 1H), 2.55 (m, 2H), 2.45–2.3 (m, 8H), 2.2 (m, 2H); [α]$_D^{22}$ +7.2° (5% in EtOH).

Anal. Calc'd for C$_{20}$H$_{22}$F$_2$N$_2$O•H$_2$O: C, 66.68; H, 6.67; N, 7.73.

Found: C, 66.51; H, 6.38; N, 7.73.

PROCEDURE 23

1-(1-Chloro-3-propanyl)-4-[bis(4-fluorophenyl)methyl]piperazine

Pentane (10 mL) was added to sodium hydride (0.50 g, 11 mmol of 50% suspension in mineral oil) and the mixture was stirred under nitrogen. The pentane was decanted. Anhydrous DMF (12 mL) was added and the suspension was cooled to 0° C. [Bis(4-fluorophenyl)methylpiperazine (2.9 g, 10 mmol) in anhydrous DMF (14 mL) was added at 0° C. within 10 min. The reaction mixture was allowed to warm to room temperature. After 1 h, the mixture was cooled to 0° C. and to the light green solution 1-chloro-3-bromopropane (5 mL, 50 mmol) in anhydrous DMF (5 mL) was added over a period of 10 min. The mixture was stirred under nitrogen at room temperature for 72 h. The solvents were evaporated in vacuo (1 mm Hg) at 50° C. The residue was triturated in methylene chloride and filtered through celite. The filtrate was washed with water (2×100 mL), dried (sodium sulfate), filtered, and the filtrate was evaporated in vacuo to give crude chloropropyl compound (3.65 g). Pentane (50 mL) was added, and on the next day the pentane insoluble solid was removed by filtration. The filtrate was evaporated in vacuo to give the title compound (2.3 g, 75%) as a clear, colorless oil. 100 MHz $^1$H NMR (CDCl$_3$) δ: 7.32 (m, 4H), 6.95 (m, 4H), 4.2 (s, 1H), 3.57 (m, 2H), 2.2–2.6 (m, 10H), 1.9 (m, 2H). DCI/MS (M+1) 361.

Anal. Calcd. for $C_{20}H_{23}ClF_2N_2$: C, 65.83; H, 6.35; N, 7.68.

Found: C, 65.59; H, 6.42; N, 7.63.

PROCEDURE 24

1-[1-(2,3-Epoxy)propyl]-4-[bis(4-fluorophenyl)methyl]-piperazine

A solution of 4,4'-difluorobenzhydrylpiperazine (28.83 g, 100 mmol) in acetonitrile (250 mL) was added to an ice cold mixture of epibromohydrin (9.1 mL, 110 mmol) and anhydrous potassium carbonate (15.2 g, 110 mmol) in acetonitrile (150 mL) over a period of 40 min. The mixture was stirred at room temperature for 100 h, filtered and the solids were washed with methylene chloride. The combined filtrates were concentrated to dryness to give an oil which was eluted through a flash chromatographic silica gel column using 2–3% methanol/methylene chloride to give the title compound as glass, 23.98 (69.6%); 300 MHz $^1$H NMR (CDCl$_3$) δ: 7.4–6.9 (m, 8H). 4.22 (s. 1H), 3.09 (br m, 1H), 2.8–2.25 (m, 12H); MS 345 (MH+).

Anal. Calcd. for $C_{20}H_{22}F_2N_2O$: C, 69.75; H, 6.44; N, 8.13; F, 11.50.

Found: C, 69.73; H, 6.49; N, 8.19; F, 11.66.

PROCEDURE 25

1-Amino-3-[4-[bis(4-fluorophenyl)methyl]-1-piperazinyl]-2-propanol

A solution of 1-[1-(2,3-epoxy)propyl]-4-[bis(4-fluorophenyl)methyl]piperazine (8.9 g, 25.8 mmol) and liquid ammonia (20 mL) in EtOH (40 mL) was heated in a teflon reaction vessel in a bomb at 110° C. for 28 h. The solution was then evaporated to dryness to give about 10 g of a glass which was purified using flash chromatography on silica gel and increasing proportions of methanol in methylene chloride to give the product as an oil which solidified upon vacuum drying, 5.7 g (61%), mp 45°–47° C. IR(neat) 3350 cm$^{-1}$; 300 MHz $^1$H NMR (CDCl$_3$) δ: 7.4–6.9 (m, 8H), 4.21 (s, 1H), 3.68 (br m, 1H) 2.8–2.2 (m, 12H); MS 362 (MH+).

Anal. Calcd. for $C_{20}H_{25}F_2N_3O$: C, 66.46; H, 6.97; N, 11.63.

Found: C, 66.21; H, 7.10; N, 11.63.

PROCEDURE 26

1-(1-Chloro-2-hydroxy-3-propanyl)-4-[bis(3,4'-trifluoromethylphenyl)methyl]piperazine•5/4 Hydrate 3,4'-Trifluoromethylphenylpiperazine (1.7 g, 4.4 mmol) was reacted as above with epichlorohydrin to give the title compound as an amber oil, 1.23 g (72%). DCI/MS (M+1) 481; 400 MHz $^1$H NMR (CDCl$_3$) δ: 7.68 (s, 1H); 7.6–7.4 (m, 7H), 4.39 (s, 1H), 3.9 (m, 1H), 3.55 (m, 2H), 2.7 (m, 2H), 2.55–2.4 (m, 8H).

Anal. Calcd. for $C_{22}H_{23}ClF_6N_2O$•5/4H$_2$O: C, 52.54; H, 5.11; N, 5.57.

Found: C, 52.48; H, 5.41; N, 5.22.

What is claimed is:

1. A compound of the formula

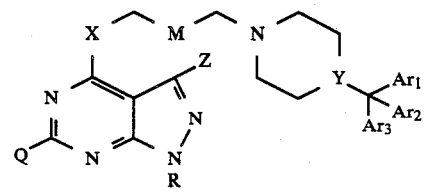

wherein X is selected from S, O;

M is selected from CH$_2$, CHOH, CHOCOR$_2$ and CHOR$_2$ wherein R$_2$ is selected from straight or branched chain C$_1$-C$_8$- lower alkyl, phenyl and substituted phenyl wherein the substituent is C$_1$-C$_4$- lower alkoxy, CF$_3$, halo and C$_1$-C$_4$- lower alkyl, NO$_2$ and CN;

Y is N, N(CH$_2$)$_n$ wherein n is 0–4, or a carbon atom having a double bond (C═) attached to the carbon atom to which Ar$_1$, Ar$_2$ and Ar$_3$ are attached; Ar$_1$, Ar$_2$ and Ar$_3$ are independently selected from hydrogen, C$_1$-C$_4$- lower alkyl, phenyl, substituted phenyl wherein the substituent is C$_1$-C$_4$- lower alkyl, C$_1$-C$_4$- lower alkoxy, CF$_3$, halo and perhalo, NO$_2$ and CN; naphthyl, pyridyl and thienyl;

Z is selected from H, CN, CO$_2$R$_3$ wherein R$_3$ is H or C$_1$-C$_4$- lower alkyl; C$_1$-C$_4$- lower alkyl, halogen and OH;

R is selected from H, C$_1$-C$_4$- lower alkyl; cyclopentyl, cyclohexyl, benzyl, C$_2$-C$_6$- lower alkenyl, C$_2$-C$_6$- lower alkynyl, tetrahydropyranyl and tetrahydrofuranyl;

Q is selected from halo, amino, C$_1$-C$_4$- lower alkyl and OH;

and the optically active isomers thereof; provided that at least one of Ar$_1$ Ar$_2$ and Ar$_3$ is aromatic and when Y is C═, only Ar$_1$ and Ar$_2$ are present.

2. A compound of claim 1 wherein X is S.

3. A compound of claim 1 wherein X is O.

4. A compound of claim 1 wherein X is S, Y is N, M is CHOH, Z is H, R is H, and Ar$_1$ and Ar$_2$ are phenyl or substituted phenyl and Ar$_3$ is H.

5. A compound of claim 1 where X is O, Y is N, M is CHOH, Z is H, R is H, and Ar$_1$ and Ar$_2$ are phenyl or substituted phenyl and Ar$_3$ is H.

6. A compound of claim 1 which is selected from (2R)-(−)-4-[1-[1-bis(4-fluorophenyl)methyl]piperazin-4-yl]-2-hydroxy-3-propanylthio]-1H-pyrazolo[3,4-d]pyrimidine and (2S)-(+)-4-[1-[1-bis(4-fluorophenyl)-methyl]piperazin-4-yl]-2-hydroxy-3-propanylthio]-1H-pyrazolo[3,4-d]pyrimidine.

7. A compound of claim 1 selected from the group consisting of 4-[2-hydroxy-3-(1-(diphenylmethyl)piperazin-4-yl)-3-propanylthio]-1H-pyrazolo[3,4-d]pyrimidine; 4-[3-[4-[bis(4-fluorophenyl)methyl]-piperazin-1-yl]-2-hydroxy-propoxy]-1-(tetrahydro-2-pyranyl)-pyrazolo [3,4-d]pyrimidine; 1-(1,2-epoxy-3-propanyl)-4-[1-(diphenylmethylpiperazin-4-yl]-2-hydroxy-3-propanylthio-1H-pyrazolo[3,4-d]pyrimidine; 4-[1-[1-[bis(-chlorophenyl)methyl]piperazin-4-yl]-2-hydroxy-3-propanylthio]-1H-pyrazolo[3,4-d]pyrimidine; and 4-[1-[1-bis(4-fluorophenyl)methyl]piperazin-4-yl]-2-hydroxy-3-propanylthio]1H-pyrazolo[3,4-d]pyrimidine.

8. A pharmaceutical composition comprising a compound of claim 1 of the formula:

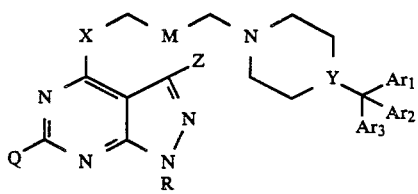

wherein X is selected from S, O; M is selected from $CH_2$, CHOH, $CHOCOR_2$ and $CHOR_2$ wherein $R_2$ is selected from straight or branched chain $C_1-C_8$- lower alkyl, phenyl and substituted phenyl wherein the substituent is $C_1-C_4$- lower alkoxy, $CF_3$, halo, $NO_2$, CN and $C_1-C_4$- lower alkyl; Y is N, $(CH_2)_n$ wherein n is 0-4, or C≡; $Ar_1$, $Ar_2$ and $Ar_3$ are independently selected from hydrogen, $C_1-C_4$- lower alkyl, phenyl, substituted phenyl wherein the substituent is $C_1-C_4$- lower alkyl, $C_1-C_4$- lower alkoxy, $CF_3$, halo and perhalo, $NO_2$ and CN; naphthyl, pyridyl and thienyl;

Z is selected from H, CN, $CO_2R_3$ wherein $R_3$ is H or $C_1-C_4$ lower alkyl; $C_1-C_4$- lower alkyl, halogen and OH;

R is selected from H, $C_1-C_4$- lower alkyl; cyclopentyl, cyclohexyl, benzyl, $C_2-C_6$ lower alkenyl, $C_2-C_6$- lower alkynyl, tetrahydropyranyl and tetrahydrofuranyl;

Q is selected from halo, amino, $C_1-C_4$- lower alkyl and OH; and the optically active isomers thereof; provided that at least one of $Ar_1$ $Ar_2$ and $Ar_3$ is aromatic and when Y is C≡, only $Ar_1$ and $Ar_2$ are present; and a pharmaceutically acceptable carrier therefor.

9. The composition of claim 8 wherein X is S.
10. The composition of claim 8 wherein X is O.
11. The composition of claim 8 wherein the compound is 4-[1-[1-bis(4-fluorophenyl)methyl]piperazin-4-yl]-2-hydroxy-3-propanylthio]1H-pyrazolo[3,4-d]pyrimidine.
12. The composition of claim 8 wherein the compound is (2S)-(+)-4-[1-[1-[bis(4-fluorophenyl)methyl]-piperazin-4-yl]-2-hydroxy-3-propanylthio]1H-pyrazolo[3,4-d]pyrimidine.
13. A method for treating heart disease which comprises administering an effective amount of a compound of claim 1 of the formula

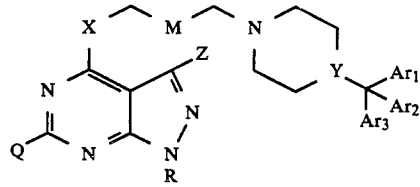

wherein X is selected from S, O; M is selected from $CH_2$, CHOH, $CHOCOR_2$ and $CHOR_2$ wherein $R_2$ is selected from straight or branched chain $C_1-C_8$- lower alkyl, phenyl and substituted phenyl wherein the substituent is $C_1-C_4$- lower alkoxy, $CF_3$, halo, $NO_2$, CN and $C_1-C_4$- lower alkyl; Y is N, $(CH_2)_n$ wherein n is 0-4, or C≡; $Ar_1$, $Ar_2$ and $Ar_3$ are independently selected from hydrogen, $C_1-C_4$- lower alkyl, phenyl, substituted phenyl wherein the substituent is $C_1-C_4$- lower alkyl, $C_1-C_4$- lower alkoxy, $CF_3$, halo and perhalo, $NO_2$ and CN; naphthyl, pyridyl and thienyl;

Z is selected from H, CN, $CO_2R_3$ wherein $R_3$ is H or $C_1-C_4$- lower alkyl; $C_1-C_4$- lower alkyl, halogen and OH;

R is selected from H, $C_1-C_4$- lower alkyl; cyclopentyl, cyclohexyl, benzyl, $C_2-C_6$- lower alkenyl, $C_2-C_6$- lower alkynyl, tetrahydropyranyl and tetrahydrofuranyl;

Q is selected from halo, amino, $C_1-C_4$- lower alkyl and OH; and the optically active isomers thereof; provided that at least one of $Ar_1$, $Ar_2$ and $Ar_3$ is aromatic and when Y is C≡, only $Ar_1$ and $Ar_2$ are present.

14. The method of claim 13 wherein the compound is selected from 4-[1-[1-bis(4-fluorophenyl)methyl]piperazin-4-yl]-2-hydroxy-3-propanylthio]1H-pyrazolo[3,4-d]pyrimidine, and (2S)-(+)-4-[1-[1-[bis(4-fluorophenyl)-methyl]piperazin-4-yl]-2-hydroxy-3-propanylthio]1H-pyrazolo[3,4-d]pyrimide.

15. The method of preventing cardiac arrythmia which comprises administering an effective amount of a compound of claim 1 of the formula:

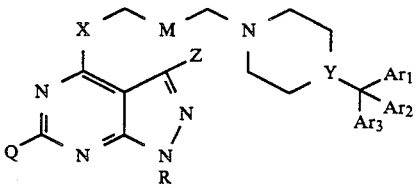

wherein X is selected from S, O; M is selected from $CH_2$, CHOH, $CHOCOR_2$ and $CHOR_2$ wherein $R_2$ is selected from straight or branched chain $C_1-C_8$- lower alkyl, phenyl and substituted phenyl wherein the substituent is $C_1-C_4$- lower alkoxy, $CF_3$, halo, $NO_2$, CN and $C_1-C_4$- lower alkyl; Y is N, $(CH_2)_n$ wherein n is 0-4, or C≡; $Ar_1$, $Ar_2$ and $Ar_3$ are independently selected from hydrogen, $C_1-C_4$- lower alkyl, phenyl, substituted phenyl wherein the substituent is $C_1-C_4$- lower alkyl, $C_1-C_4$- lower alkoxy, $CF_3$, halo and perhalo, $NO_2$ and CN; naphthyl, pyridyl and thienyl;

Z is selected from H, CN, $CO_2R_3$ wherein $R_3$ is H or $C_1-C_4$ lower alkyl; $C_1-C_4$- lower alkyl, halogen and OH;

R is selected from H, $C_1$–$C_4$- lower alkyl; cyclopentyl, cyclohexyl, benzyl, $C_2$–$C_6$- lower alkenyl, $C_2$–$C_6$- lower alkynyl, tetrahydropyranyl and tetrahydrofuranyl;

Q is selected from halo, amino, $C_1$–$C_4$- lower alkyl and OH; and the optically active isomers thereof; provided that at least one of $Ar_1$ $Ar_2$ and $Ar_3$ is aromatic and when Y is C=, only $Ar_1$ and $Ar_2$ are present.

16. The method of claim 15 wherein the compound is selected from 4-[1-[1-bis(4-fluorophenyl)methyl]piperazin-4-yl]-2-hydroxy-3-propanylthio]1H-pyrazolo[3,4-d]pyrimidine (2S)-(+)-6-[1-[bis(4-fluorophenyl)methyl]piperazin-4-yl]-2-hydroxy-3-propanylthio]1H-pyrazola[3,4-d]-pyrimidine.

* * * * *